United States Patent [19]

Kondo

[11] 4,221,705
[45] Sep. 9, 1980

[54] NOVEL PEPTIDE TYPE ANTIBIOTIC AND THE PROCESS FOR THE PRODUCTION THEREOF

[75] Inventor: Shigeji Kondo, Sendai, Japan

[73] Assignee: Kakenyaku Kako Co., Ltd., Tokyo, Japan

[21] Appl. No.: 971,497

[22] Filed: Dec. 20, 1978

[30] Foreign Application Priority Data

Dec. 28, 1977 [JP] Japan ................................. 52-157416

[51] Int. Cl.² ..................... C07C 103/52; A61K 37/00
[52] U.S. Cl. .............................. 260/112.5 R; 424/177
[58] Field of Search ................... 260/112.5 R; 424/177

[56] References Cited

FOREIGN PATENT DOCUMENTS 1227670  5/1970  Japan ...................................... 424/177

OTHER PUBLICATIONS

Tulloch, Trans. Br. Mycol. Soc. 66, (3) 407–411 (1976).
Kondo, Tohoku J. Exp. Med. (1977), 122, 403–404.

*Primary Examiner*—Delbert R. Phillips
*Attorney, Agent, or Firm*—Kane, Dalsimer, Kane, Sullivan and Kurucz

[57] ABSTRACT

A straight chain peptide type antibiotic K 582 M which consists of arginine 1, threonine 1, tyrosine 1, ornithine 2, hydroxyarginine m, lysine n as amino acid constituents and the process for the production of K 582 M comprising culturing a K 582 M producing microorganism.

2 Claims, 7 Drawing Figures

NOVEL PEPTIDE TYPE ANTIBIOTIC AND THE PROCESS FOR THE PRODUCTION THEREOF

BACKGROUND OF THE INVENTION

The present invention relates to K 582 M and the process for the production thereof.

More specifically the present invention relates to a cultured medium obtained by culturing a K 582 M producing microorganism belonging to Genus Metarhizium and a mixture of K 582 M-A and -B obtained from said cultured medium and furthermore K 582 M-A and K 582 M-B obtained by separating from said mixture of K 582 M-A and B as well as the process for the production of the said products.

SUMMARY OF THE INVENTION

The present invention provides a straight chain peptide type antibiotic K 582 M including K 582 M-A and K 582 M-B, which have an antibiotical effect, tumor-inhibiting effect and other biological effects as well as the process for the production thereof. K 582 M herein described is a novel straight chain, peptide type antibiotic composed of arginine: 1, threonine: 1, tyrosine: 1, ornithine: 2, hydroxyarginine: m and lysine: n as amino acid constituents as well as salts thereof. 582 M-A hereinafter described is K 582 M in which m of hydroxyarginine and n of lysine correspond to 1 and 1, respectively, and K 582 M-B is K 582 M in which m of hydroxyarginine and n of lysine correspond to 2 and 0, respectively.

DETAILED DESCRIPTION OF THE PREFERRED EMBODIMENTS OF THE INVENTION

Figure 1:
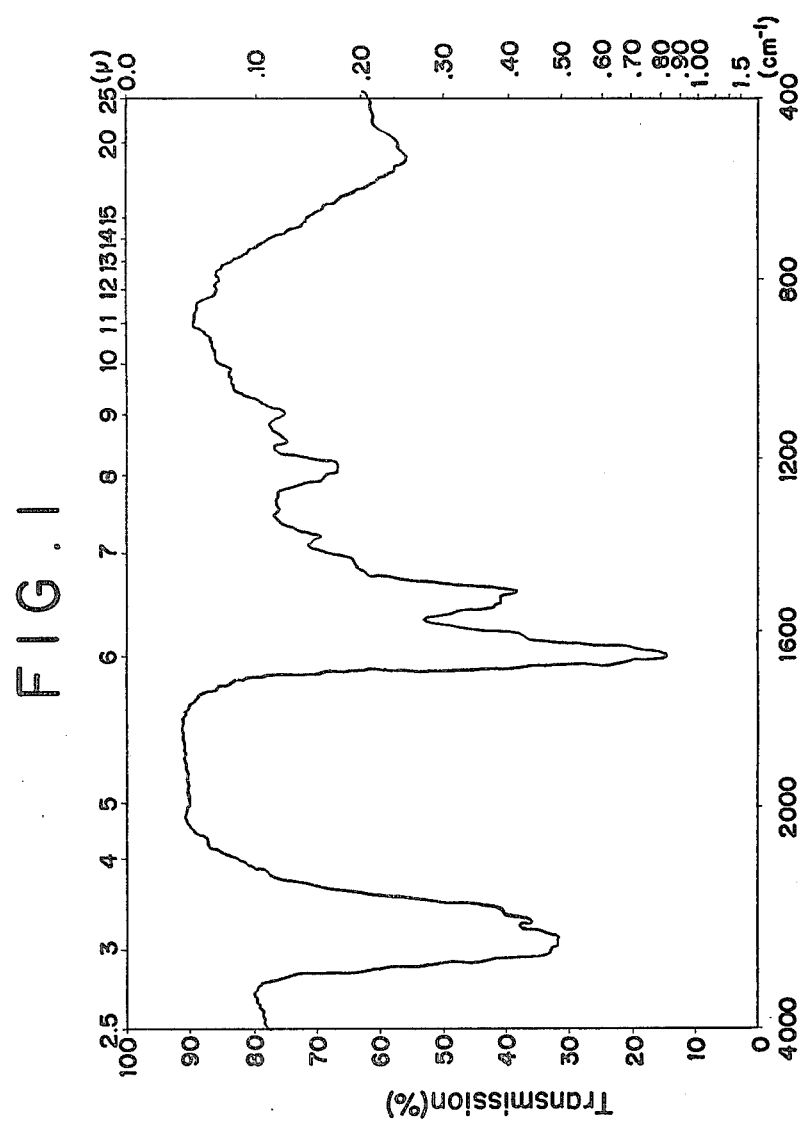
FIGS. 1 and 2 show IR-spectrum of K 582 M-A (hydrochloride) and K 582 M-B (hydrochloride) respectively.

In the cultured medium of a strain belonging to Genus Metarhizium utilized as K 582 M producing microorganism, for example, *Metarhizium anisopliae* (Metsch) Sorok. var. anisopliae 582 M, there is deposited substances effective for inhibiting the growth of various true fungi, especially Candida and the other yeasts and also substances effective for virus such as polio, influenza, etc. and effective for transplanted tumors of experimental animals.

The present invention has been accomplished by the successful isolation of these two substances having similar characteristics as novel peptide type active substance from said cultured medium.

The strain *Metarhizium anisopliae* (Metsch) Sorok. var. anisopliae 582 M has been deposited with Kogyogijutsuin-Biseibutsu-Kogyo-Gijutsu-Kenkyujo (Japan) as FERM-P No. 4217 on Nov. 25, 1977 and with ATCC as ATCC No. 20500 on Dec. 27, 1977. The toxonomic characteristics of this Strain are set forth under:

Macroscopic observation:

The growth of the colony on malt extract agar is quick and it reaches to a diameter of 4.5–5.0 cm after two weeks at 25° C. It exhibits somewhat sheaf form. It is flat or on occasion radially crumped. Colour of the colony is from dark grayish green to yellowish green at the spore-forming central part and white at the margin. Sometimes green parts and white parts are mingled or formed in stripe. Its back side represents from algal yellow to cream colour and no secreting fluid is recognized. It has a stimulating odor like as that of some belonging to Genus Streptomyces.

Microscopic observation:

Mycelium is colourless and has ceptums and branches. Conidiophore is short, colourless and has septums. It shapes in single or branched form. Rather than single form, it shapes endly in finely branched form like as Penicillium and finally forms a mass by close assembling of firelands (branching of pointed end). Cylindrical construction consisting of conidium developes on the part such as loose layer. The fireland is long and slender cylindrical form, which is colourless and its pointed ends become slender. Further at the ends thereof there are connected with long chains of conidium and constitute a long cylindrical assembly by connecting each other. Conidium is monocellular flat herospore type and represents pale yellowish green colour tone, which is shaped in cylindrical or long elipsoidal form and four corners are roundish. Length and width are 4.0–8.0μ and 2.0–2.5μ respectively, but usually in the range of 5.0–7.0μ. Candida is composed in centripetally to form multiple chains and by sticking each other to establish grayish green tall cylinder.

Its properties on various agar culture mediums are shown, as under:

| | Aspect on the various agar culture medium (28° C.) | | | | | |
|---|---|---|---|---|---|---|
| | Growth conditions | | | Formation of Spore | | |
| | Growth | Shape | Margin | Winkling | and its colour | Pigment | Water drop |
| Czapek-pepton-Agar | good | pillow form | ciliary | winkled | from yellowish green to dark green | produce | none |
| Czapek-Dox-Agar | good | button form | small lobe | winkled | yellowish green to dark green | produce | none |
| Saburo-Agar | good | pillow form | ciliary | winkled | yellowish green to dark green | produce | none |
| Corn-Meal-Agar | poor | mycelium trial in flatness | teeth-form in irregular set | none | dark green | none | none |
| Malt-Agar | somewhat poor (widely extended) | mycelium is thin flatness | wave | none | grayish green to dark green | produce | none |
| Potato- | somewhat | mycelium is | ciliary | none | dark green | produce | none |

-continued

| | | Aspect on the various agar culture medium (28° C.) | | | | | |
|---|---|---|---|---|---|---|---|
| | | Growth conditions | | | Formation of Spore | | |
| | Growth | Shape | Margin | Winkling | and its colour | Pigment | Water drop |
| Dextrose-Agar | poor | thin flat | | | | | |
| Gelatin-Agar | somewhat poor | mycelium is thin flat | wave | none | dark green | none | none |
| Ordinary Agar | somewhat poor | mycelium is thick snow flakes form | wave | none | none | none | none |

Observed after 20 days

In the culture according to the invention general knowledges with respect to the cultivation of fungi may be applied. As for culture medium and nutritive sources there may be used various kinds thereof, however, as carbon sources sugars such as dextrose, sucrose, levulose, mannose, glycerin, starchs, maltose, xylose, lactose, molasses, mannan are preferably used. As for nitrogen sources inorganic salts such as sodium nitrate, ammonium nitrate, ammonium chloride, etc. as well as organic nitrogen sources such as bouillon, peptone, corn steep liquar, yeast extract, soya bean flour, peanut-flour, amino acids, etc. may be used. The other suitable inorganic salts and assistant agents and so on may be used as occasional demands.

As for the culture method, even when it is cultured on a solid culture medium, the production of K 582 M can be recognized, however, it is most advantageous to culture in a liquid culture medium for the large scale production.

The cultivation is carried out aerobically at a temperature of between 20° and 37° C., preferably between 28° and 30° C. and a pH value of between 3.0 and 8.0, preferably between 5.4 and 5.6. If required there may be added a defoamer at a suitable stage.

To collect K 582 M from the cultured medium after completion of the fermentation, there may be applied a process generally used for collecting the fermentation products, for example, precipitation process by a hydrophilic organic solvent, for example, ethanol, acetone, etc., a precipitation process by an organic acid, for example, picric acid, flavianic acid, etc., precipitation process by a chemical substance, for example, phosphotungustic acid, sodium pentachlorophenol, benzoaldehyde, etc., extraction process by methanol or by various kind of active absorbent and also purification process by applying ion-exchange carrier, molecular sieve chromatography, density orientation process, counter current distribution process, fractionation process by salts, solvents or metal ions, electrophoresis process, isolation process by the formation of a complex substance and a suitable combination thereof to obtain the objective substance.

As an example, the objective substance may be easily separated by a process, combining precipitation with purification by an ion-exchange resin, which process comprises steps of filtration by the addition of a filter aid, treatment of the filtrate with an acidic ion-exchange resin or a basic ion-exchange resin and then elution with an acid or alkali.

The concentrate thus obtained by the use of the ion-exchange resin is further concentrated, then added with suitable amounts of ethanol and acetone to produce crude powder of K 582 M-A and B mixture. Crude powder thus obtained is further treated with methanol, alumina, active carbon, molecular sieve chromatography and so on to provide a purified product.

K 582 M-A and B mixture thus obtained contains said K 582 M-A and K 582 M-B and shows properties as if both are exist together in physiochemical properties thereof and also has physiological effects such as antibiotic activity, tumor inhibiting activity, acceleration and inhibition effects of immurity, interferon-inducing effects, and so on.

The purified product thus obtained or the cultured broth or eluate obtained by ion-exchange carrier, etc. from the cultural broth can be treated with various chromatographic process, for example, by the use of polyacrylamidegel, CM-Cephadex, etc. to isolate K 582 M-A and K 582 M-B. From K 582 M-A and K 582 M-B each thus obtained can be produced more purified products by utilizing various kind of purification respectively.

Figure 2:
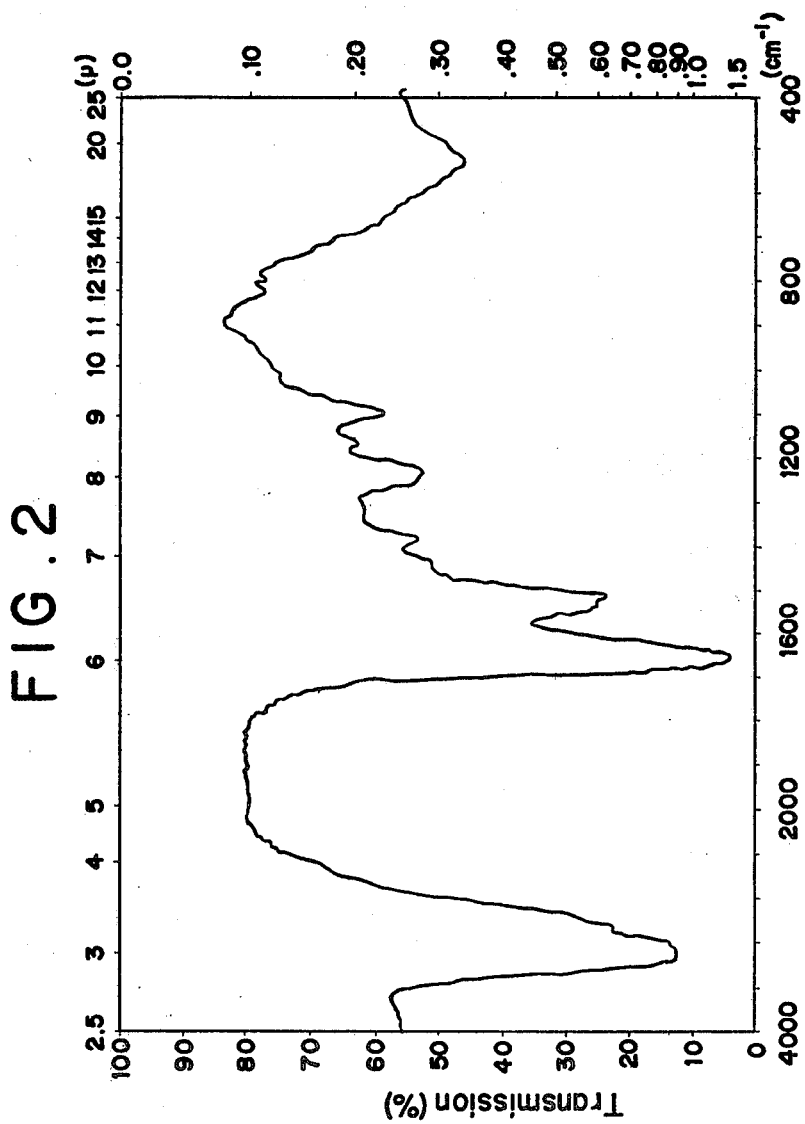
Figure 3:
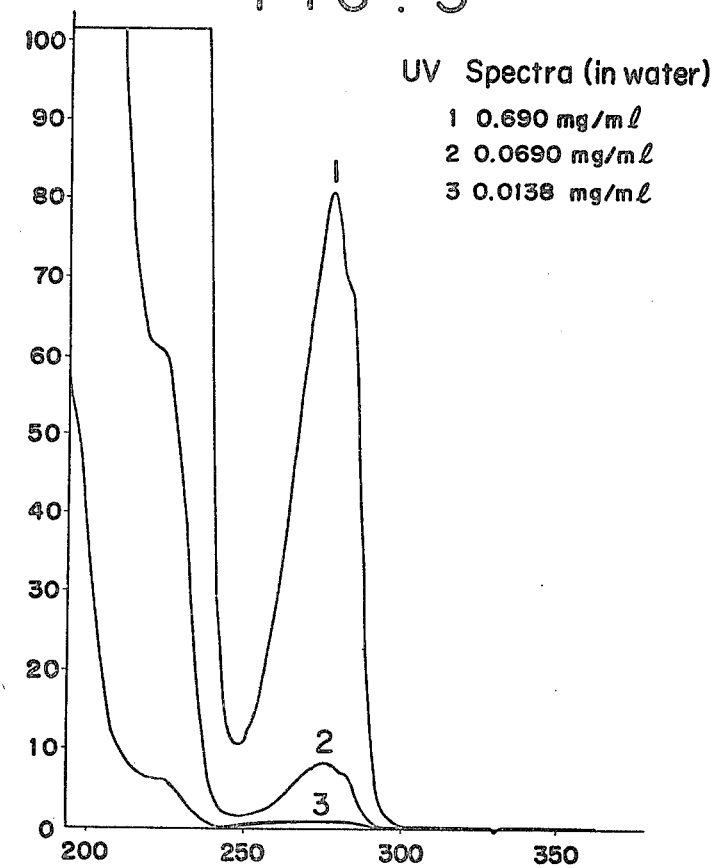
FIGS. 3 and 4 represent UV-spectrum of K 582 M-A (hydrochloride) and K 582 M-B (hydrochloride) respectively.
Figure 4:
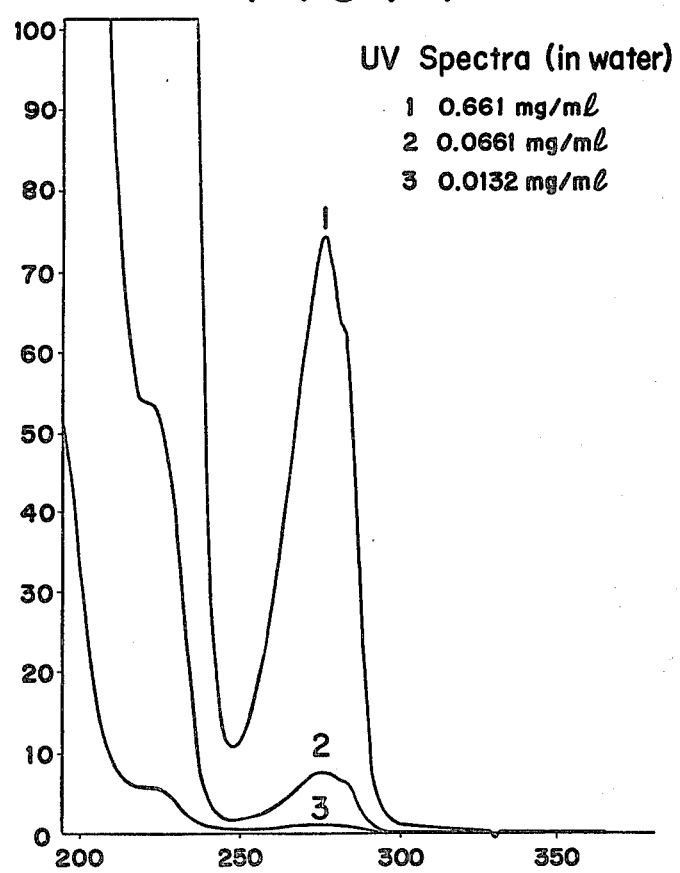
Figure 5:
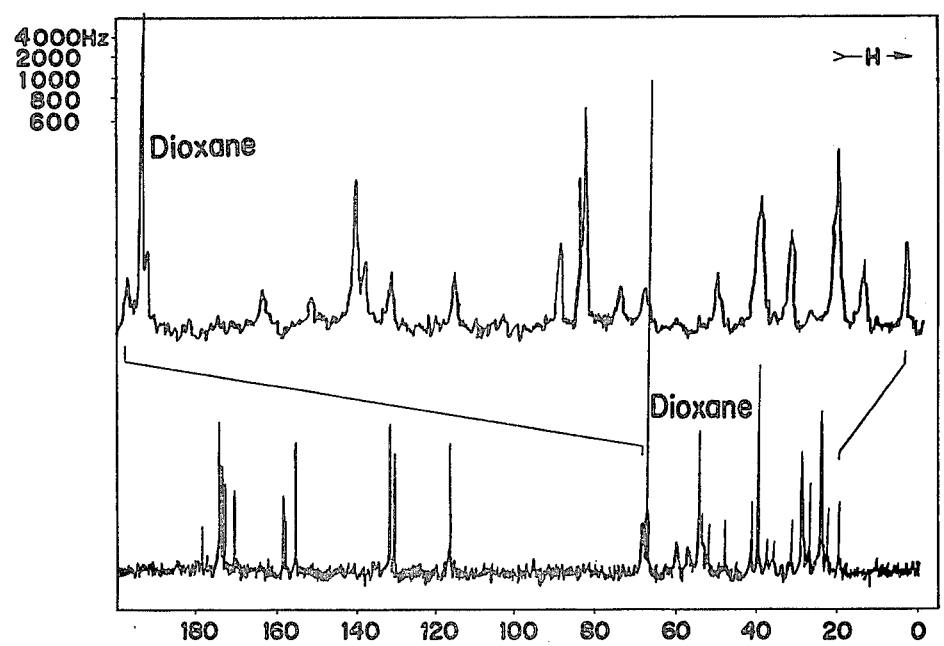
FIGS. 5 and 6 represent $C^{13}$-NMR-spectrum of K 582 M-A (hydrochloride) and K 582 M-B (hydrochloride) respectively.
Figure 6:
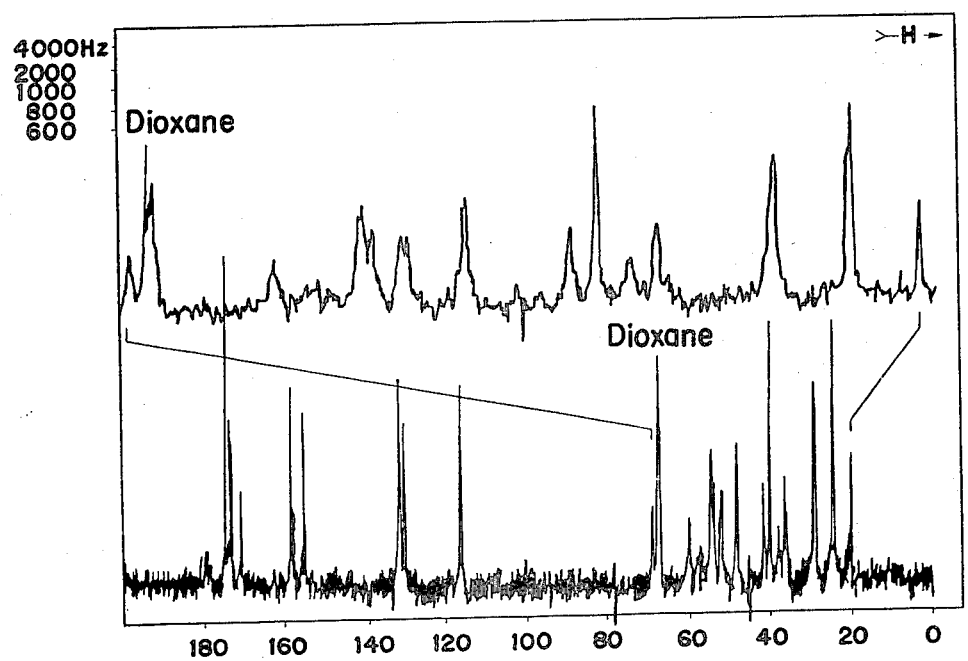

Physiochemical properties of K 582 M-A and K 582 M-B thus obtained are indicated in the following:

| | K 582 M - A (HCl salt) | K 582 M - B (HCl salt) |
|---|---|---|
| 1. | Elementary Analysis (%) <br> C: 39.35 <br> H: 7.24 <br> N: 18.03 <br> C: 14.83 | C: 36.25 <br> H: 6.61 <br> N: 18.62 <br> C: 14.06 |
| 2. | Molecular Weight (Measured the undermentioned three methods, however, since these methods give wide error in the under-mentioned molecular weight range, the characteristics of the substances according to the invention are not to be restricted by the under-mentioned measured molecular weight values) | |
| | About 1300 (Gel filtration process) | About 1200 (Gel-filtration process) |
| | About 1300 (Freezing point method) | About 1220 (Freezing point method) |
| | About 1200 (Vapour pressure method) | About 1200 (Vapour pressure method) |
| 3. | Melting Point <br> 192°–198° C. (decomp.) | 197°–203° C. (decomp.) |
| 4. | Specific Rotary Power (Since these values change widely according to the conditions of measurement, the characteristics of the substances according to the invention are not to be restricted.): | |
| | $[\alpha]_D^{22} = +0.2°$ (C = 1%,H$_2$O) | $[\alpha]_D^{22} = +0.6°$ (C = 1%,H$_2$O) |
| 5. | Infrared Spectrum | |
| | K 582 M - A (hydrochloride) | K 582 M - B (hydrochloride) |
| | FIG. 1 | FIG. 2 |
| 6. | Ultraviolet Absorption Spectrum | |
| | FIG. 3 | FIG. 4 |
| 7. | C$^{13}$-NMR Spectrum | |
| | FIG. 5 | FIG. 6 |
| 8. | Solubility | |
| | ① Hydrochloride <br> Easily soluble in water, methanol. sparlingly soluble in ethanol. Insoluble in ether, petroleum-ether, butanol, chloroform, benzene. | same as left |
| | ② Sulphate (Especially solubility of Sulphates are shown.) | |

| | K 582 M - A (HCl salt) | K 582 M - B (HCl salt) |
|---|---|---|
| | Easily soluble in water, sparingly soluble in methanol. Insoluble in the other solvents. | same as left |
| 9. Colour Reaction: | Ninhydrin Reaction + Xanthoprotein Reaction + Millon's Reaction + Sakaguchi Reaction + Pauly's Reaction + Molisch Reaction − Tollen-Orcin Reaction − Na-nitropruside Reaction − | same as left |
| 10. Nature (as free base) | Basic substance | same as left |
| 11. Colour | White amorphous powder | same as left |
| 12. Precipitation Reaction | Precipitation occurs by the addition of undermentioned reagents: Phosphor tungstate, pictric acid, flavianic acid, pentachlorophenol, benzaldehyde | |
| 13. Stability | Stable in acidic and neutral reaction. Somewhat unstable in basic reaction. | same as left |
| 14. Amino Acid Sequence | K582M-A L-ARG—L-ARG(OH)—D-ORN—L-THR—D-ORN—L-Lys—D-TYR K582M-B L-ARG—L-(ARG(OH)—D-ORN—L-THR—D-ORN—L-ARG(OH)—D-TYR | |

Biological activities of K 582 M-A and K 582 M-B, both of which are HCl salt.

1. Antibiotical effects of K 582 M-A and K 582 M-B (Dilution method)

| Microorganisms tested | Minimum growth inhibiting concentration (mc g/ml) | |
|---|---|---|
| | K 582 M - A | K 582 M - B |
| Candida albicans | 0.2 | 0.4 |
| Candida tropicalis | 0.2 | 0.4 |
| Candida pseudo-tropicalis | 0.2 | 0.4 |
| Candida utilis | 0.2 | 0.4 |
| Candida guilliermondii | 0.2 | 0.4 |
| Candida krusei | 0.2 | 0.4 |
| Saccharomyces cerevisiae Br-60 | 0.2 | 0.4 |
| Saccharomyces rouxii bottlucue | 0.2 | 0.4 |
| Zygosaccharomyces salsus | 0.2 | 0.4 |
| Willia anomala | 0.2 | 0.4 |
| Torulaspora delbruckii | 0.2 | 0.4 |
| Rhodotorula lupra | 0.2 | 0.4 |
| Mycotorula | 0.2 | 0.4 |
| Debaryomyces kloecheri | 0.2 | 0.4 |
| Pullularia pullulans | 0.2 | 0.4 |
| Proteus OX-19 | 20 | 40 |
| Bacillus subtilis | >100 | >100 |
| Staphylococcus aureus 209-P | >100 | >100 |
| Escherichia coli | >100 | >100 |
| Shigella sonnei | >100 | >100 |
| Bacillus lutea Hata | >100 | >100 |
| Bacillus mycoides | >100 | >100 |
| Mycobacterium cymote | >1000 | >1000 |
| Mycobacterium Smegmatis | >1000 | >1000 |
| Mycobacterium H$_{37}$RV | >1000 | >1000 |
| Trichohyton asteroide | >1000 | >1000 |
| Trichohyton lpulam | >1000 | >1000 |
| trichomonas waginalis | >1000 | >1000 |

As can be seen from above, K 582 M-A and K 582 M-B show strong antibiotical activity against Candida micro-organisms and other yeasts.

2. Acute Toxic characters of K 582 M-A and K 582 M-B

| Route | | Mouse LD$_{50}$ mg/kg | |
|---|---|---|---|
| | | K 582 M - A | K 582 M - B |
| Intravenous Administration | ♂ | 120–144 | 24.1–34.8 |
| | ♀ | 144–1728 | 24.1–34.8 |
| Intraperitoneal Administration | ♂ | above 300 | 43.2–57.2 |
| | ♀ | above 300 | 43.2–57.2 |
| Subcutaneous Administration | ♂ | 320 or more | 86.8–104 |
| | ♀ | 320 or more | 104–125 |
| Oral Administration | ♂ | above 6000 | 2400–3000 |
| | ♀ | above 6000 | 2400–3000 |

3. Tumor-inhibiting effects of K 582 M-A and K 582 M-B (a) Tumor-inhibiting effects with the tumor carrying rats Groups each consisting of ten rats of Donryu origin (female: 150–200 g) are transplanted $10^7$ of ascites liver-cancer cells AH 44 and AH 66 respectively in the tail vein, then after the elapse of 72 hours K 582 M-A or K 582 M-B is administered orally in a dose of 30 mg/kg continuously for 10 times and after 60 days existence rate of rats is determined. As can be seen from the following Table, in every tumor-carrying rats group there is recognized strong tumor-inhibiting effects as compared with the control by only supplying of diet.

| Animal group | Existence Rate (%) | | |
|---|---|---|---|
| Tumor Cell | Control | K 582 M - A | K 582 M - B |
| AH 44 | 0 | 100 | 50 |
| AH 66 | 0 | 80 | 40 |

(b) Tumor-inhibiting effects with Tumor-carrying mouse

Groups each consisting of 10 mice of dd origin (female: 20 g±1.0 g) are transplanted each $10^6$ of Ehrlich's ascites cancer cells, sarcoma cells S-180 and leukemic ascites cancer cells SN 36 respectively in peritoneal cavity of mouse and after 24 hours elapse of time K 582 M-A or K 582 M-B is administrated in a dose of 35 mg/kg/day for 10 days in peritoneal cavity of mouse respectively. The results of this experiment in the cases of the administrations of the products of the invention showed strong tumor-inhibiting effects (Existence rate after 60 days) as shown in the following Table, whereas in the case of the control group, mice have all died after about 20 days.

| Mice group | Existence Rate of Mice (%) | | |
|---|---|---|---|
| Tumor Cell | Control | K 582 M - A | K 582 M - B |
| Sarcoma cells S-180 | 0 | 90 | 90 |
| Ehrlich's ascites Cancer cells | 0 | 70 | 80 |
| Leukemic ascites Cancer cells SN 36 | 0 | 80 | 70 |

4. The other biological effects (a) Effects against the immune system of a living body It has now been found as results of various experiments that K 582 M - A and K 582 M - B give effects on immunity of living body (both in humoral and cellulorr). Especially it has now also been found that the substances of the invention have both accelerating and inhibiting effects against the immune system in the hemolysine titer method by the SRBC (sheep rod blood corpuscles) administration and accordingly an example of said effects of K 582 M - B will be shown as mentioned under.

Groups each consisting of 5-10 female mice of ddI origin are administered with K 582 M - B in a dose of 25 mg/kg as well as 2.5 mg/kg per day for 4 days by intraperitoneally and $4 \times 10^8$ of SRBC are transplanted in veins of tail and the administration of K 582 M - B is continued for further 4 days and after completion of the administration antibody values in blood are measured. A group of 25 mg/kg of administration showed 77% of antibody value based on the control group and a group of 2.5 mg/kg of administration showed 234% of antibody value based on the control and groups of higher concentration administration showed tendencies of inhibiting of immunity and groups of lower concentration administration showed a tendency of accelerating of immunity.

(b) Action of interferone inducer-like effects

We have now found that when K 582 M - A or K 582 M - B is administered in a living body, it induces higher units of interferon in blood. As an example, said effects as to K 582 M - B will be stated as mentioned under. A mouse of dd origin is administered with K 582 M - B orally in a dose of 2.5 mg/kg and interferone titer in the blood is measured with the elapse of time and after 25 hours there is showed a maximum value of 1280 Dilution units. This shows a very strong interferone inducing effects of this substance. Such effects are also recognized with the other animals such as domestic fowl, rabbit, dog, swine, etc. In the influenza virus infection experiments of mouse, when 2 mg/kg of K 582 M - B is orally administered to mouse at 12 or 24 hours prior to the infection, there is shown 30-40 percent of prolongation of life.

The characteristics of K 582 M - A and K 582 M - B as stated above will clearly demonstrate that these substances are novel substances obtained by us. When K 582 M - A (H₂SO₄ salt) or K 582 M - B (H₂SO₄ salt) is used, the similar results are obtained.

The present invention will be further illustrated by the following examples, however, it is not to be restricted only in these and so long as the various properties of the substances according to the invention have clearly been teached, it is obvious for those skilled in the art that even if there were not practically described with respect to the scope of the invention, the objects of the invention can also be attained by applying the variation or altered means.

The present invention will further be illustrated by the following Examples.

EXAMPLE 1

(a) 200 ml of liquid culture medium (pH about 6) having a composition of 3.0% glucose, 1.0% polypeptone, 0.2% sodium nitrate, 0.1% potassium dihydrogen phosphate, 0.05% potassium chloride, 0.05% magnesium sulphate, 0.01% ferrous sulphate is inoculated with Metarhizium anisopliae (Metsch.) Sorok. var. anisopliae 582 M (Bikoken FERM-P No. 4217, ATCC No. 20500) and shaking cultivation is carried out at 30° C. for 14-20 days.

(b) The procedure of Example 1 (a) is repeated, except that instead of 1.0% of polypeptone 0.1% of amino acid (glycine, asparagine, arginine, histidine, alanine and others are separatedly applied) is added.

EXAMPLE 2

5l of filtrate of the cultured broth obtained in Example 1 is filtered under the addition of Hiflo-supercel.

After adjusting the pH value in 6.0-7.0 the obtained filtrate is passed through a column of ion-exchange resin IRC-50 (H⁺, Na⁺ mixed type) having 20 mm of inner diameter and 500 mm of height to adsorb the objective substances thereon. The column is washed with water, then 500 ml of 1.0 N HCl is passed through in a flow rate of 10 ml/min to elute the objective substances. The eluate is adjusted at the pH value of 6.0 and then concentrated under a reduced pressure. The concentrate is allowed to stand over night at 35° C. under the addition of sodium pentachlorophenol to result a precipitation of pentachlorophenolate of K 582 M - A and B mixture. The obtained pentachlorophenolate of K 582 M - A and B mixture is washed with water, then dissolved in butyl acetate and the obtained solution is extracted twice with diluted hydrochloric acid solution of pH value of 2.0-3.0 to obtain aqueous solution of K - 582 M - A and B mixture (HCl salt). The aqueous solution is washed several times with butyl acetate and the aqueous layer is adjusted to pH 4.0 and then concentrated under reduced pressure. The residue is added with a sufficient amount of ethanol to precipitate K 582 M - A and B mixture (HCl salt). Thus, 5.0 g of crude powder of K 582 M - A and B mixture (HCl salt) is obtained.

The obtained powder is again dissolved in methanol, and, by adding a sufficient amount of aceton and ethanol to the methanol solution, K 582 M - A and B mixture (HCl salt) is precipitated, which is collected by filtration. K 582 M - A and B mixture (HCl salt) thus obtained is dissolved in methanol and purified by utilizing a column of Cephadex LH-20 to give 4.0 g of K 582 M - A and B mixture (HCl salt) as white powder.

EXAMPLE 3

1 g of K 582 M - A and B mixture (HCl salt) obtained by the procedure described in Example 2 is dissolved in 5 ml of water and the aqueous solution is treated with chromatography by utilizing a column (inner diameter 26 mm; height 1200 mm) of Biogel P-2 (100-200 mesh). That is, by using 0.1 M NaCl aqueous solution, it is eluted in the rate of 30 ml/hr, and at first the fraction of K 582 M - A (HCl salt) and then secondly the fraction of K 582 M - B (HCl salt) are obtained. The eluates A and B thus obtained are each again treated with chromatography, and concentrated under reduced pressure. A mixture of acetone and ethanol (4:1) is added to the obtained residue for precipitation and after drying the obtained precipitates are extracted repeatedly with methanol. The methanol solution is concentrated under reduced pressure and the residue is precipitated by the addition of a mixture of acetone and ethanol (4:1), and dried to provide K 582 M - A (HCl salt) powder or K 582 M - B (HCl salt) powder. After the obtained powder A and powder B are each dissolved in a small amount of 80% methanol, and the methanol solution is purified by desaltation with chromatography by utilizing the Column (inner diameter 26 mm, height 1200 mm) of Cephadex LH-20, the obtained eluate is concentrated under reduced pressure and the residue is precipitated with a mixture of acetone and ethanol (4:1). Precipitates are dried and thus 0.41 g of K 582 M - A (HCl salt) (yield 41.0%) and 0.35 g of K 582 M - B (HCl salt) (yield 35.0%) are obtained respectively.

EXAMPLE 4

1 g of K 582 M - A and B mixture (HCl salt) obtained by the procedure in Example 2 is dissolved in 5 ml of water and the aqueous solution is treated with chromatography by using a column (inner diameter 20 mm, height 500 mm) of CM-Cephadex C-25 (100–200 mesh). Chromatography is carried out at first with 0.1 M phosphoric acid buffer (pH 6), then 0.4 M NaCl solution and further 0.9 M NaCl solution as eluting solvent. After the eluting is changed to 0.9 M NaCl solution, there is eluted at first K 582 M - A (HCl salt) and then K 582 M - B (HCl salt). Eluates of K 582 M - A (HCl salt) and K 582 M - B (HCl salt) are each concentrated, dried, extracted repeatedly and then the methanol-soluble part is concentrated and the residue is precipitated by the addition of a mixture of acetone and ethanol (4:1) to obtain K 582 M - A (HCl salt) and K 582 M - B (HCl salt) in powder form respectively. Powder A and powder B thus obtained are each dissolved in a small amount of 80% aqueous methanol and the methanol solution is purified by desaltation with chromatography using a column of Cephadex LH-20. After concentration under reduced pressure the eluate is precipitated by the addition of a mixture of acetone and ethanol (4:1) and the precipitates are dried to obtain 0.40 g of purified K 582 M - A (HCl salt) (yield 40.0%) and 0.43 g of purified K 582 M - B (HCl salt) (yield 43.0%), respectively.

EXAMPLE 5

5l of cultured medium obtained by the procedure described in Example 1 is filtered under the addition of 100 g of Hiflo-super-cel. The obtained filtrate is adjusted to pH value of 5.0–6.0, concentrated to a volume of 1/10–1/20, removed the inorganic salts contained therein, again concentrated to dryness, and extracted with 200 ml of methanol for several times. The combined extract is concentrated, which is repeatedly extracted with methanol under reducing the amount of methanol one after another, and the extracts are completely dissolved in a small amount of water and the obtained aqueous solution is treated by chromatography with a column (inner diameter 50 mm, height 1000 mm) of Biogel P-2 (100–200 mesh). That is, it is eluted with 0.1 M NaCl -solution (flow rate 30 ml/hr) to obtain at first the fraction of K 582 M - A (HCl salt) and then the fraction of K 582 M - B (HCl salt). The eluates of these fractions are each purified by desaltation according to the procedure described in Example 3 (methanol extraction, addition of a mixture of acetone and ethanol, Cephadex LH-20 column treatment) to obtain 1.4 g of dried K 582 M - A (HCl salt) and 1.2 g of dried K 582 M - B (HCl salt), respectively.

EXAMPLE 6

5l of cultured medium obtained according to the procedure described in Example 1 is filtered under the addition of Hiflo-super cell. After concentration under reduced pressure the filtrate is filtered from the separated substance and is adjusted at a pH value of 5.0–7.0 and then passed through in a column (inner diameter 20 mm, height 1000 mm) of CM-Cephadex C-25 (100–200 mesh) to adsorb the objective substances thereon. Then the column is eluted at first with 0.1 M phosphoric acid buffer solution having pH value of 6.0, then 0.4 M NaCl solution and further 0.9 M NaCl solution. After the elute-solution is changed to 0.9 M NaCl solution, at first K 582 M - A (HCl salt) and secondly K 582 M - B (HCl salt) are eluted. These fractionated eluates each containing K 582 M - A (HCl salt) and K 582 M - B (HCl salt) respectively are concentrated, dried, desalted by the procedure described in Example 4 (methanol) extraction, addition of a mixture of acetone and ethanol, treatment with Cephadex LH-20 column) and dried and thus there is obtained 1.2 g of dried K 582 M - A (HCl salt) and 1.3 g of dried K 582 M - B (HCl salt), respectively.

EXAMPLE 7

Figure 7:
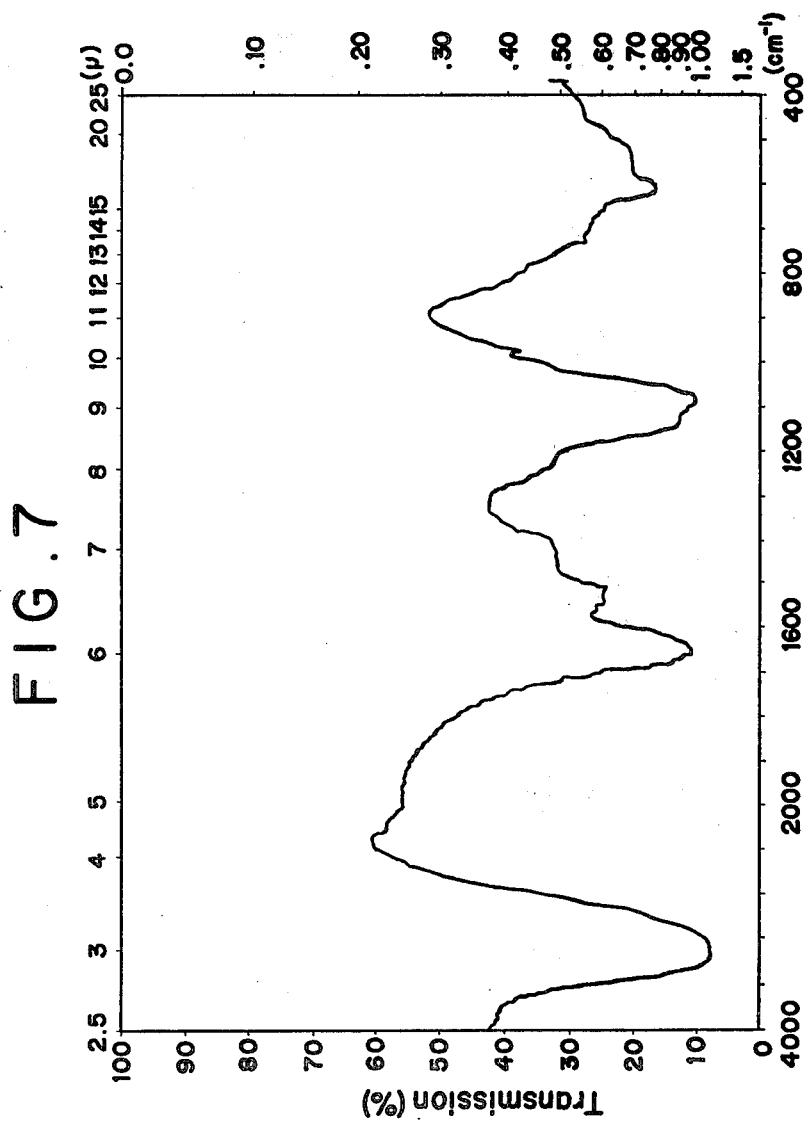
FIG. 7 represents IR-spectrum of K 582 M-A (sulphate).

2 g of K 582 M - A (hydrochloride) obtained by the method of Example 3 or 4 is dissolved in 5 ml of distilled water and applied to a column of IRC-50 (4×25 cm). After the column is washed with 400 ml of distilled water K - 582 M - A (sulfate) is eluted with 1 N $H_2SO_4$. The eluate containing K 582 M - A (sulphate) is added with IRA-400. After adjusting the mixture at pH value of 6.0, it is filtrated and then concentrated. The concentrate is added with a mixture of acetone: EtOH (4:1) and the separated precipitates are filtered off. The obtained K 582 M - A (sulphate) is treated with desalting refining by the use of Cephadex column LH-20 (2.2×80 cm). Distilled water is used for elution. 1.4 g of K 582 M - A (sulphate) is obtained by freeze-drying of the resulted eluate. Its IR-spectrum is shown in FIG. 7. Similarly K 582 M - A (sulphate) can be obtained by the treatment proportionately with the above stated process.

EXAMPLE 8

Amino acid sequence of K 582 M - A

After our study on the amino acid analysis with respect to K 582 M - A we have now found that K 582 M - A consists of arginine 1,γ-hydroxyarginine 1, ornithine 2, threonine 1, lysine 1 and tyrosine 1 and the C-terminal amino acid is tyrosine (hydrazine decomposition method).

Using Edman elimination method, the amino acid sequence of K 582 M - A is successively analysed from the N-terminal. That is, 3 mg of K 582 M - A is dissolved in 0.5 ml water and 1.0 ml pyridine and the pH is adjusted at 9.0–9.5 by the addition of 1 N NaOH. After 100 μl of phenylisothiocyanate is added and the flask is substituted with nitrogen gas, the flask contents are maintained at 40° C. for 90 minutes. After washed with benzene, they are freeze-dried and the flask is substituted with nitrogen gas, charged with 200 μl of trifluoroacetic acid, and maintained at 40° C. for 15 minutes.

After removal of trifluoroacetic acid, a portion of residue is taken out and hydrolyzed at 110° C. for 22 hours by the action of 6 N HCl to analyze the amino acid. As a result, it is confirmed that an arginine is split off from K 582 M - A, that is, the N-terminal amino acid is arginine.

By using the above-mentioned Edman alimination method, the amino acid sequence of from the N-terminal amino acid to the third amino acid therefrom in K 582 M - A is analyzed successively and it is confirmed to be arginine-γ-hydroxyarginine-ornithine.

After heating at 55° C. for 24 hours in trifluoacetic acid followed by removal of trifluoroacetic acid, 50 mg of K 582 M - A is subjected to high pressure filterpaper electrophoresis. In addition to K 582 M - A, two ninhydrin-positive substances are recognized and one of these is positive on Sakaguchi's reaction. When the trifluoroacetic acid decomposition product is gel-filtered at 1 ml/fraction with Sephadex LH-20 Column (Column size: 18×840 mm; Solvent: 80% methanol), there are eluted K 582 M - A and a ninhydrin-positive and Sakaguchi's reaction-positive substance as a mixture in the fractions No. 136–154.

There is also eluted a ninhydrin-positive and Sakaguchi's reaction-positive substance as a single substance in the fractions No. 156–164. After the analysis of this substance eluted at the fractions No. 156–164, it was found to consist of arginine 1 and γ-hydroxy arginine 1. After concentration, the fractions No. 136–154 is adsorbed on CM-cellulose column equilibrated with 0.01 M ammonium acetate (Column size: 17×160 mm) and then subjected to gradient elution using 2 M-NaCl aqueous solution at 1.5 ml/fraction to elute a ninhydrin-positive and Sakaguchi's Reaction-negative substance in the fractions No. 220–233. There is also eluted K 582 M - A in the fractions No. 302–328. The fractions No. 220–230 is desalted with Sephadex LH-20 (80% methanol) and after amino acid analysis there is obtained the amino acid composition of ornithine 2, threonine 1, lysine 1 and tyrosine 1. Further by the hydrazine decomposition method it was found that the C-terminal amino acid is tyrosine.

The fractions No. 220–230 is used to successively analyze the amino acid sequence from the N-terminal, that is, 2 mg of the fractions No. 220–233 is dissolved in 0.2 ml water and 0.3 ml pyridine and adjusted at a pH value of 9.0–9.5. 100 μl of phenyl isothiocyanate is added and the flask is substituted with nitrogen gas and maintained at 40° C. for 90 minutes. After washed with benzene, it is freeze-dried, and the flask is substituted with nitrogen gas, charged with 200 μl of trifluoroacetic acid, and maintained at 40° C. for 15 minutes. After removal of trifluoroacetic acid, a portion of the residue is taken out and hydrolyzed at 110° C. for 22 hours by the action of 6 N HCl to analyze the amino acid. As a result, it is confirmed that an ornithine is split off from the fractions No. 220–233, that is, the N-terminal amino acid of the fractions No. 220–233 is ornithine.

By using the above-mentioned Edman elimination method, the amino acid sequence of the fractions No. 220–233 is analyzed in succession starting from the N-terminal, it is confirmed to be ornithine-threonine-ornithine-lysine-tyrosine.

From the above-mentioned results, it is determined that the amino acid sequence of K 582 M - A is arginine-γ-hydroxyarginine-ornithine-threonine-ornithine-lysine-tyrosine.

EXAMPLE 9

Amino acid sequence of K 582 M - B

Amino acid analysis of K 582 M - B shows that its amino acid constituents are arginine 1, γ-hydroxyarginine 2, ornithine 2, threonine 1 and tyrosine 1, and hydrazine decomposition indicates that the C-terminal amino acid is tyrosine.

Using Edman elimination method, the N-terminal amino acid of K 582 M - B is determined. That is, 1 mg of K 582 M - B is dissolved in 0.2 ml water and 0.3 ml pyridine and adjusted at a pH value of 9.0–9.5 by the addition of 1 N NaOH. Then, 100 μl of phenyl isothiocyanate is added and the flask is substituted with nitrogen gas and maintained at 40° C. for 90 minutes. After washed with Benzene, it is freeze-dried, and the flask is substituted with nitrogen gas, charged with 200 μl trifluoro acetic acid, and maintained at 40° C. for 15 minutes. After removal of trifluoroacetic acid, a portion of the residue is taken out and hydrolyzed at 110° C. for 22 hours by the action of 6 N HCl to analyze the amino acid. As a result, it is confirmed that an arginine is split off from K 582 M - B, that is, the N-terminal amino acid is arginine.

100 mg of K 582 M -B is heated in trifluoroacetic acid at 40° C. for 9 hours. After removal of trifluoroacetic acid, it is subjected to gel-filtration using Sephadex LH-20 Column (Column size: 18×970 mm; Solvent: water), in which after 105 ml of initial eluate is cut, fractions are collected at a rate of 1.15 ml/fraction. As a result, there are eluted a mixture in the fractions No. 40–83 fractions, and a dipeptide consisting of arginine 1 and hydroxy-arginine 1 as amino acid constituents in the fractions No. 84–92, as well as tyrosine in the fractions No. 114–134. After concentration, the fractions No. 40–83 is adsorbed on a CM-cellulose Column (Column size: 15×600 mm) equirabted with 0.01 M ammonium acetate and then treated with gradient elution at 1.0 ml/fraction using 1 M NaCl. In the fractions No. 191–204 there is eluted a tetrapeptide which was found by the amino acid analysis as being consisting of ornithine 2, threonine 1, and hydroxy arginine 1.

Using Edman elimination method, fractions No. 191–204 is analyzed under the same conditions as in K 582 M - B to clarify the amino acid sequence successively. As a result, the fractions No. 191–204 is determined to be a tetrapeptide having the amino acid sequence of ornithine-threonine-ornithine-γ-hydroxy arginine.

From the above-mentioned results, the amino acid sequence of K 582 M - B is finally determined to be arginine-γ-hydroxy arginine-ornithine-threonine-ornithine-γ-hydroxy arginine-tyrosine.

What is claimed is:

1. The polypeptide arginine-γ-hydroxyarginine-ornithine-threonine-ornithine-lysine-tyrosine.

2. The polypeptide arginine-γ-hydroxyarginine-ornithine-threonine-ornithine-γ-hydroxyarginine-tyrosine.

* * * * *

UNITED STATES PATENT AND TRADEMARK OFFICE
CERTIFICATE OF CORRECTION

PATENT NO. : 4,221,705
DATED : September 9, 1980
INVENTOR(S) : Shigeji Kondo

It is certified that error appears in the above—identified patent and that said Letters Patent is hereby corrected as shown below:

Col. 5, line 65; - "Baccilus" should read -- Sarcina --

Col. 6, line 20; - "Intravenous $\overset{+}{\delta}$" should read -- Intravenous $\overset{\uparrow}{\delta}$ --

Col. 6, line 22; - "Intraperitoneal $\overset{+}{\delta}$" should read -- Intraperitoneal $\overset{\uparrow}{\delta}$ --

Col. 6, line 24; - "Subcutaneous $\overset{+}{\delta}$" should read -- Subcutaneous $\overset{\uparrow}{\delta}$ --

Col. 6, line 26; - "Oral $\overset{+}{\delta}$" should read -- Oral $\overset{\uparrow}{\delta}$ --

Col. 6, line 60; - "35" should read -- 25 --

Col. 7. line 21; - "rod" should read -- red --.

Signed and Sealed this

Twenty-third Day of December 1980

[SEAL]

Attest:

SIDNEY A. DIAMOND

Attesting Officer

Commissioner of Patents and Trademarks